(12) United States Patent
Handschuck et al.

(10) Patent No.: US 8,201,441 B2
(45) Date of Patent: Jun. 19, 2012

(54) METHOD AND DEVICE FOR DETERMINING THE DEGREE OF HARDNESS OF SEMISOLID MATERIALS

(75) Inventors: Bernhard Handschuck, Dahlewitz (DE); Helmut Eilers, Dahlewitz (DE)

(73) Assignee: Petrotest Instruments GmbH & Co. KG, Dahlewitz (DE)

( * ) Notice: Subject to any disclaimer, the term of this patent is extended or adjusted under 35 U.S.C. 154(b) by 445 days.

(21) Appl. No.: 12/445,941

(22) PCT Filed: Oct. 10, 2007

(86) PCT No.: PCT/EP2007/060784
§ 371 (c)(1),
(2), (4) Date: Apr. 17, 2009

(87) PCT Pub. No.: WO2008/046774
PCT Pub. Date: Apr. 24, 2008

(65) Prior Publication Data
US 2010/0313638 A1    Dec. 16, 2010

(30) Foreign Application Priority Data

Oct. 17, 2006  (DE) .................. 10 2006 049 813

(51) Int. Cl.
*G01N 3/42*  (2006.01)
(52) U.S. Cl. ............................. 73/82; 73/83
(58) Field of Classification Search .............. None
See application file for complete search history.

(56) References Cited

U.S. PATENT DOCUMENTS

| | | | | |
|---|---|---|---|---|
| 4,245,496 A * | 1/1981 | Napetschnig | ............ | 73/83 |
| 5,074,983 A * | 12/1991 | Eltoukhy et al. | ............ | 204/192.13 |
| 5,553,486 A * | 9/1996 | Bonin | ............ | 73/105 |
| 5,886,253 A * | 3/1999 | Joustra | ............ | 73/84 |
| 6,026,677 A * | 2/2000 | Bonin | ............ | 73/105 |
| 6,142,010 A | 11/2000 | Merck et al. | | |
| 7,302,831 B2 * | 12/2007 | Moyse et al. | ............ | 73/81 |
| 2005/0115310 A1 * | 6/2005 | Wu | ............ | 73/81 |
| 2009/0056427 A1 * | 3/2009 | Hansma et al. | ............ | 73/82 |

FOREIGN PATENT DOCUMENTS

| | | |
|---|---|---|
| DE | 3830815 A1 | 3/1990 |
| DE | 4021178 A1 | 1/1992 |
| DE | 29711490 U1 | 1/1998 |
| DE | 10257170 A1 | 6/2004 |
| EP | 1061354 A | 12/2000 |
| FR | 2823307 A | 10/2002 |

* cited by examiner

*Primary Examiner* — Andre Allen
(74) *Attorney, Agent, or Firm* — Aaron Wininger; Perkins Coie LLP

(57) ABSTRACT

An apparatus and a method allows a determination of the degree of hardness of semisolid materials with a higher accuracy and a simultaneously lower sensitivity with respect to electronic and mechanical disruptions.

Figure 1:
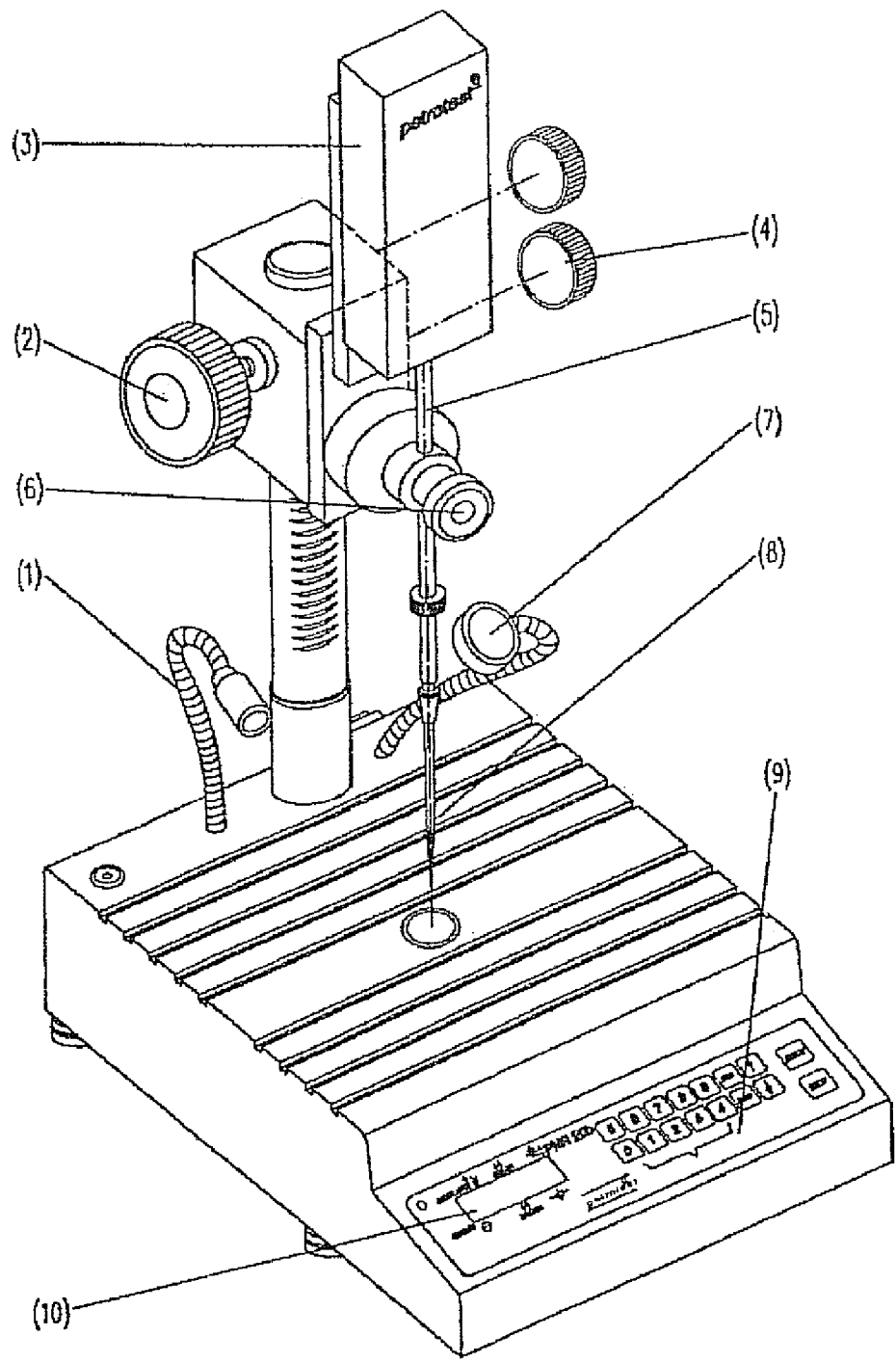

An adjusted force value ($F_{Ber}$) is determined prior or during a downward movement of a force/path sensor (20) and the force difference ($\Delta F_{32} - \Delta F_{51}$) is determined between the adjusted force value ($F_{Ber}$) and respective measured force value ($\Delta F_{32} - \Delta F_{51}$) and a zero time ($t_{41}$) is determined, wherein the position (21, $s_{41}$) of the measuring body (5, 8) at the zero time ($t_{41}$) is used as the exact starting position (21, $s_{41}$) of the surface of the material to be measured (22).

21 Claims, 5 Drawing Sheets

METHOD AND DEVICE FOR DETERMINING THE DEGREE OF HARDNESS OF SEMISOLID MATERIALS

The present invention relates to a method and a device for determining the degree of hardness of semisolid materials, in particular the present invention relates to a penetrometer and a method for measuring the degree of hardness of pavement such as asphalt or a method for measuring the degree of hardness of lubricants.

Semisolid material such as asphalt and/or bitumen are used in road construction among others. Asphalt represents a technically manufactured mixture of bitumen and mineral compounds apart from its rare natural appearance. Asphalt may be manufactured with different degrees of hardness for miscellaneous requirements by variation of binding agents and mineral compounds as well as their added amounts.

There the asphalt shall comply with those requirements which are established by principals and agents, road users, tax payers and residents. These requirements are in particular safety and driving comfort, i.e. planarity, grip, lightness of the asphalt, cost effectiveness, i.e. durability, crack security, deformation resistance, aging resistance, easy and short repair, low priced commodities, mixture-fitting and compaction with common and simple methods as well as noise reduction.

The bitumen within the asphalt undergoes a significant stress due to temperature and traffic load. Domestic asphalt surfaces cool down to −30° C. due to the application of salt during winter, and domestic asphalt surfaces reach temperatures of +50° C. due to incident solar radiation during summer. The degree of hardness is an important parameter for the characterization of the properties of bitumen. Relatively soft bitumen tends to generate flange grooves during summer while relatively hard bitumen tends to generate cracks during winter. Therefore, the exact determination of the hardness of bitumen is an important means of quality control.

The method of penetration pursuant to ASTM D 5, IP 49, DIN EN 1426, formerly: DIN 52010 is internationally used for the determination of the degree of hardness of semisolid test materials. In this connection a specified measuring body comprising a falling rod and a penetration body penetrates the test material under its own weight, wherein the measuring body is specified by its weight and its dimensions. The penetration depth in the test material represents its hardness which is reflected in the notation of the corresponding species of the bitumen ("B80" means 80/10 mm penetration depth). The apparatus for positioning and triggering the measuring body and for measuring the penetration depth in the test material is called penetrometer, the related measurement method is called penetration.

A precondition for the comparability of measuring results is the compliance with the specification and the exact positioning of the measuring body in the starting position prior to the penetration. This means that the penetration body (e.g. a penetration needle) will be positioned directly above the surface, as in the ideal case having an indefinitely small contact point with the test material. In conventional apparatuses, the starting position is for example approached by careful lowering of the measuring body by means of level adjustment until the tip of the penetration body contacts the surface of the test material, wherein the downward movement of the measuring body is carried out by a user by visual observance. The penetration itself is started by unlocking of the fixed measuring body (comprising falling rod and penetration body) from said starting position. In this connection, the measuring body penetrates the test material by its own weight. The measuring body is then fixed in its new position after a predetermined penetration time. According to ASTM D 5, IP 49, DIN EN 1426, the penetration time amounts to 5 s. The penetration depth is the result of the penetration and is used as a parameter for determining of the degree of hardness.

The required adjustment of the starting position is inevitably afflicted with errors when using the conventionally known apparatuses. The reason for said errors is the manual adjustment of the starting position under (subjective) observance by a user. In this connection, the measuring body is lowered using a hand wheel. The touch-down is then found by visual observance of the user.

An aggravating aspect is that e.g. according DIN EN 1426 a penetration measurement is carried out in a tempering liquid and therefore the point of touch-down needs to be found "under water". The incident light is only marginally reflected in case the test material is bitumen. The bad visibility conditions result in a restricted or degraded perception of the user. Mirrors, light sources (lamps) and optical means are used in the prior art for improving the visibility conditions. In this connection, lenses and spot lights may be used for the formation of shades of the tip approaching the surface of the test material. However, these measures cannot guarantee an exact determination of the starting position which means that the determination of the hardness of the test material is afflicted with errors.

An erroneous starting position (touch down error) has the following impact on the measurement results for the determination of the degree of hardness:

in case the tip of the measuring body does not touch the surface of the test material, i.e. the downward movement of the measuring body is stopped too early, the measuring body will supposedly penetrate too deep into the test material due to the fact that the drop height is too large.

in case the tip of the measuring body already penetrates the surface of the test material when being in the starting position, i.e. the downward movement is stopped too late, the measuring body will penetrate the test material too little in the following penetration measurement.

Furthermore, DE 40 21 178 A1 discloses a method for determining the hardness of semisolid materials by measuring the penetration depth of a falling measuring body into the test material, wherein the measuring body is vertically moved down by means of an electric motor, a lifting rod and further elements. A prior measurement for the determination of the zero point (starting point) in order to bring the measuring body into a predetermined starting position (i.e. a predetermined drop height) is neither disclosed nor necessary as the drop height only marginally contributes to the penetration force of the measuring body. In fact, the measuring body shall be disposed close above the surface in order to minimize the impact of the drop height.

Furthermore, DE 38 30 815 A1 discloses a method for measuring and testing the hardness of a testing body, wherein a measuring body falls onto a test surface not under its own weight but the measuring body is put onto the surface of the test body under different test forces F1 and F2. In this connection, a relatively large preload (up to 20%) of the test force is applied and the starting position is determined using extrapolation. The application of such a force would however result in a falsification of measurement results during the measurement of the hardness of semisolid materials.

Furthermore, DE 102 57 170 B4 discloses a method for the determination of hardness of semisolid materials, wherein a force/path sensor connected to the measuring body is lowered into the test material prior to the penetration measurement such that the test material will only be elastically deformed when the measuring body contacts the test material, and the exact starting position for the measuring body above or on the test material is determined according to at least two force/path values and the measuring body is adjusted to this starting position prior to the penetration measurement. This method provides an automated determination of the starting position which eliminates subjective errors. The relatively large mass which acts upon the force/path sensor is however disadvantageous as it results in an increased sensitivity for interferences, such as vibrations and the like.

It is therefore the object of the present invention to provide an apparatus and a method for determining the hardness of semisolid materials which have a high accuracy for the measurement of hardness of semisolid materials in comparison to the prior art and a simultaneously low sensitivity for electronic and/or mechanical interferences.

This object is solved by the features in the characterizing portion of claim 1 (method claim) and the features in the characterizing portion of claim 14 (device claim) in connection with the features in the corresponding preambles. Preferred embodiments of the invention are contained in the dependent claims.

A particular advantage of the present invention is that the determination of the degree of hardness of semisolid test materials may be carried out according to the method of the present invention and with the apparatus according to the present invention in a more reliable and a more simple way than according to the prior art (DE 102 57 170 B4).

According to the present invention, a force/path sensor is lowered prior to the penetration measurement from a starting position to a return point, wherein an adjusted force value is determined prior or during the downward movement, wherein a force difference between the adjusted force value and the currently measured force value in determined for a plurality of times (preferably more than 10, at least 2 times) and the point in time at which the measuring body contacts the semisolid material (zero time) is determined such that at least one of the following criteria i)-iii) is met:

i) the force differences of consecutive measurements have the same algebraic sign effective from the zero time and the time difference between the zero time and one of the consecutive measurements exceeds a predetermined time limit, ii) the force differences of consecutive measurements have the same algebraic signs effective from the zero time and the force difference of a measurement after the zero time exceeds a predetermined force value, iii) the force differences of consecutive measurements have the same algebraic sign effective from the zero time and a path difference between the zero time path value and one of the consecutive measurements exceeds a predetermined path limit, wherein the position of the measuring body at the zero time is used as the starting position of the surface of the material to be tested.

Preferably a time interval is divided into a plurality of points in time for the determination of an adjusted force measurement value wherein the time interval is located after the start of the downward movement of the measuring body until the arrival of the return point, wherein the respective force values are measured for a given number of consecutive measuring times during which the measuring body is located above the semisolid material and an adjusted force value is determined as an arithmetic mean of the measured force values. Furthermore the adjusted force value is additionally determined in accordance with the lowering velocity of the measuring body. According to an alternative preferred embodiment of the method of the present invention a reference value is used for the determination of the adjusted force value. Preferably the reference value is selected in accordance with the weight and the lowering velocity of the measuring body.

Preferably a step motor is used for lowering the measuring body into the test material. Preferably, a test material, for which the degree of hardness is to be determined, is used which comprises a needle penetration value ranging from 5 to 500 according to ASTM D5. Engineer standards with such needle penetration values are: ASTM D5, ASTM D217, IP50, ISO2137 and ASTM D5329. Preferably, the lowering of the measuring body into the test material is carried out such marginally that only an elastic deformation results in the test material due to the penetration of the measuring body up to the return point.

According to an alternative preferred embodiment of the method according to the present invention a test material having a working penetration value ranging from 50 to 500 according to ASTM D217 is used. Preferably the measuring body is lowered such into the test material that the test material is elastically deformed due to the penetration of the measuring body up to the return point.

Preferably the time limit, the force limit or the path limit for the criteria i)-iii) is determined in accordance with the test material and/or device parameters. Preferably criterion ii) and at least one of criteria i) and iii) have to be met at the same time. Preferably all of criteria i)-iii) have to be met at the same time.

The penetrometer according to the present invention comprises a measuring body, a force/path sensor, means for a vertical movement of the measuring body and means for analysis of the measurement values of the force/path sensor and for vertical movement of the measuring body, wherein the measuring body comprises a falling rod and a penetration body (penetration needle), wherein the measuring body is fixed by an interlock, wherein the interlock is supported over the test material, and wherein the force/path sensor is connected with the measuring body and the analysis means and the control means comprise a data transmission to the force/path sensor and to the means for vertical movements for the measuring body, wherein the analysis means and the control means comprises a means for determination of an adjusted force value for a plurality of measurements (preferably more than 10, at least 2 measurements) and a means for determination of a force difference between the adjusted force value and the respective measured value, wherein the analysis means and the control means are furthermore adapted for the determination of a zero time, for which at least one of the following criteria iv)-vi) is met:

iv) the force differences of consecutive measurements have the same algebraic sign effective from the zero time and the time difference between the zero time and of the consecutive measurements exceeds a predetermined time limit, v) the force differences of consecutive measurements have the same algebraic signs effective from the zero time and the force difference of a measurement after the zero times exceeds a predetermined force value, and vi) the force differences of consecutive measurements have the same algebraic sign effective from the zero time and a path difference between the zero time path value and one of the consecutive measurements exceeds a predetermined path limit.

Preferably the analysis means and the control means are adapted such that the position of the measuring body at the zero time is used as starting position of the surface of the test material and the measuring body is adjusted to this position prior to the measurement of the degree of hardness.

Preferably a time interval is divided into a plurality of points in time for the determination of an adjusted force measurement value wherein the time interval is located after the start of the downward movement of the measuring body until the arrival of the return point, wherein the respective force values are measured for a given number of consecutive measuring times during which the measuring body is located above the semisolid material and an adjusted force value is determined as an arithmetic mean of the measured force values. Furthermore the adjusted force value is additionally determined in accordance with the lowering velocity of the measuring body. According to an alternative preferred embodiment of the method of the present invention a reference value is used for the determination of the adjusted force value.

Preferably the reference value is selected in accordance with the weight and the lowering velocity of the measuring body.

Preferably the time limit, the force limit or the path limit for the criteria iv)-vi) is determined in accordance with the test material and/or device parameters. Preferably the analysis means and the control means are adapted such that the criterion v) and at least one of the criteria iv) and vi) are met at the same time for the determination of the zero time. In a very preferred embodiments all criteria i)-iii) are met at the same time.

Preferably the force/path sensor is arranged inside the falling rod. Therefore it is possible to reduce unwanted masses which influence the force sensor.

Preferably the force/path sensor is arranged in a lower portion of the falling rod, and more preferably the force/path sensor is arranged directly above the clamping for the penetration body. The penetration body is preferably formed as a penetration needle. The power supply which is necessary for the force/path sensor as well as the resulting measuring signals from the force/path sensor may be transmitted via electrical contacts or contactlessly via electromagnetic waves to the analysis and control means. The signal transmission shall not be afflict the penetration due to unwanted friction and therefore the contacting preferably (automatically) pivots away after the adjustment of the starting position but before the penetration measurement.

To this end, the force/path sensor preferably comprises a first electrical contact for data transmission and the analysis and control means comprises a second electrical contact, wherein the electrical contacts are arranged side by side and the second electrical contact is connected with a means for horizontal movement of the second electrical contact in order for contacting and decontacting with the first electrical contact. Preferably the second electrical contact of the analysis and control means is arranged on a pivoting cantilever, wherein the cantilever is adapted to realise a contacting and a decontacting, respectively, with the first electrical contact by a pivoting movement.

According to an alternative preferred embodiment of the penetrometer according to the present invention, means for wireless transmission between the force/path sensor and the analysis and control unit and/or between the analysis and control unit and the means for vertical movements of the measuring body are provided. Preferably the means for wireless data transmission between the force/path sensor and the analysis and control unit comprises a transponder, wherein the transponder is integrated within the force/path sensor or wherein the transponder is integrated in the falling rod and connected with the force/path sensor.

Preferably the means for vertical movement of the measuring body is a step motor. Preferably the analysis and control unit is a computer or is formed of a plurality of separate modules.

The invention shall be explained in the following in more detail for a preferred embodiment which is at least partly depicted in the figures.

Figure 2:
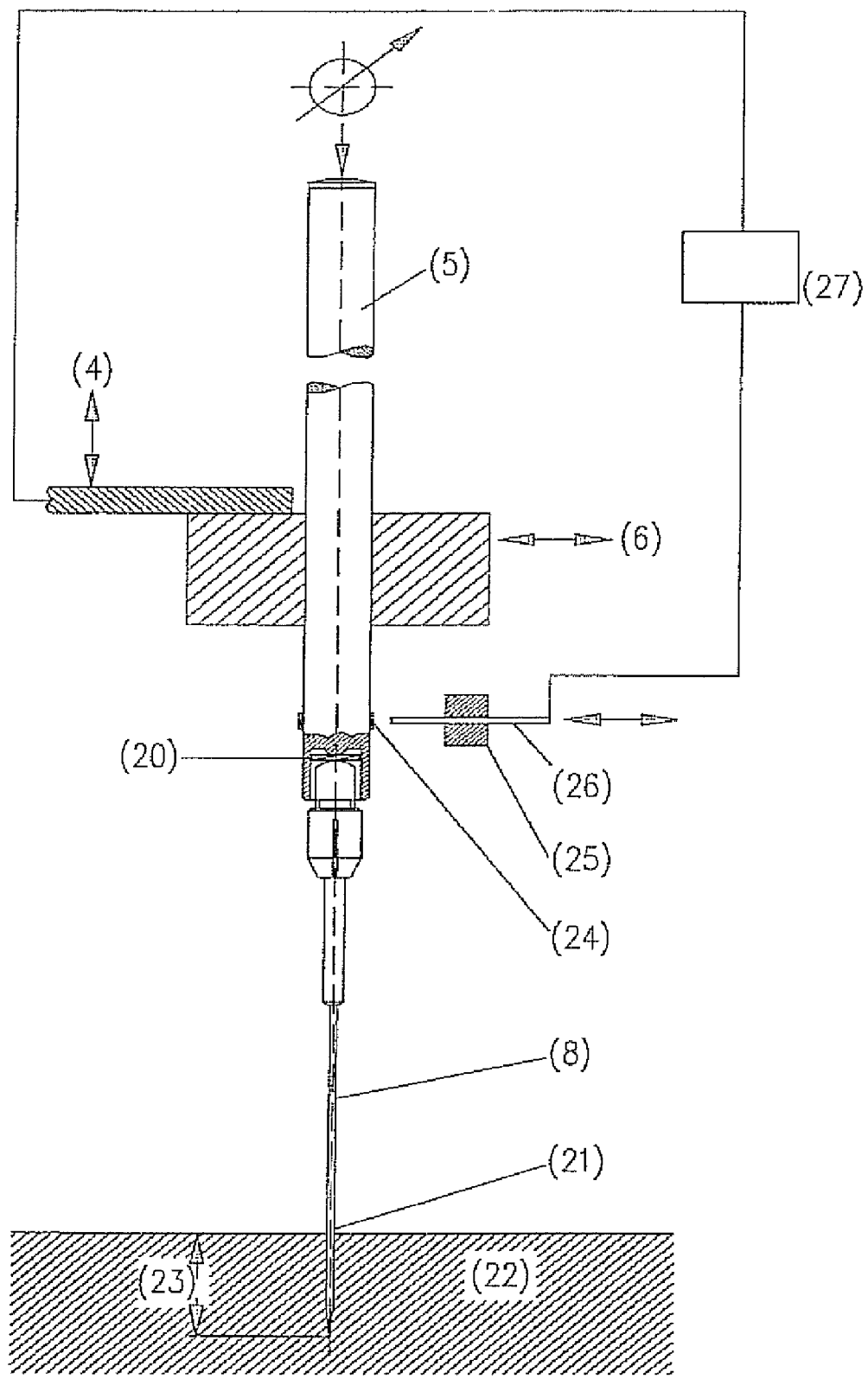
Figure 3:
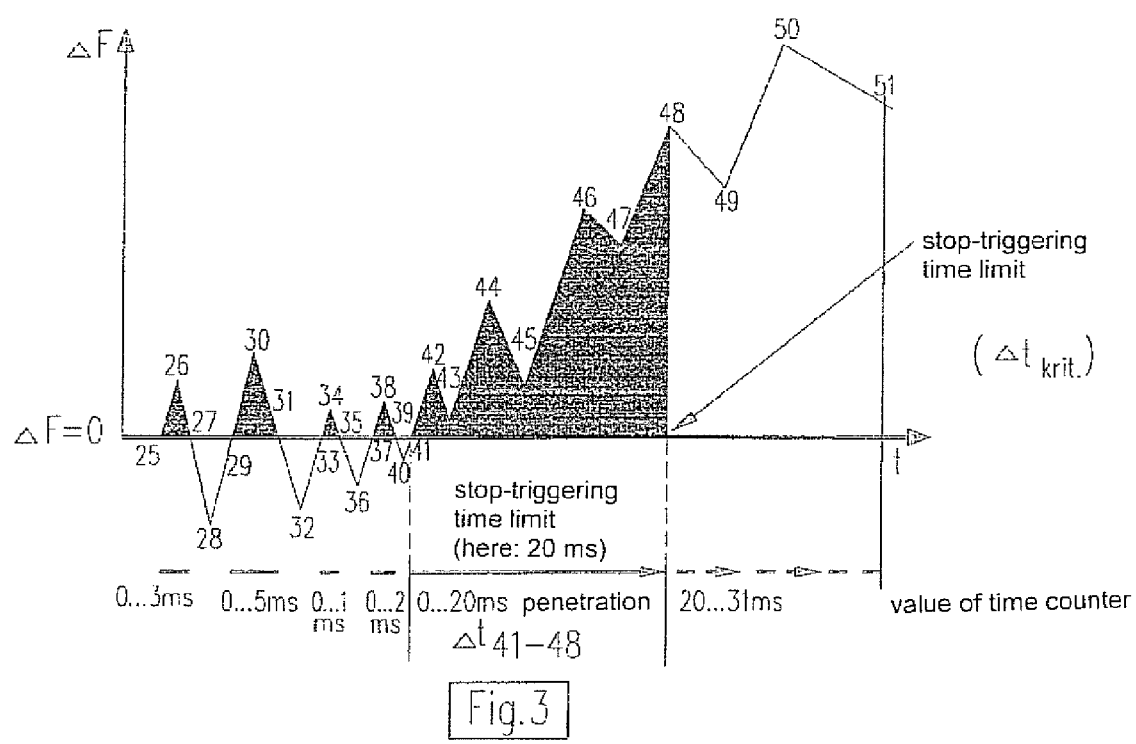
Figure 4:
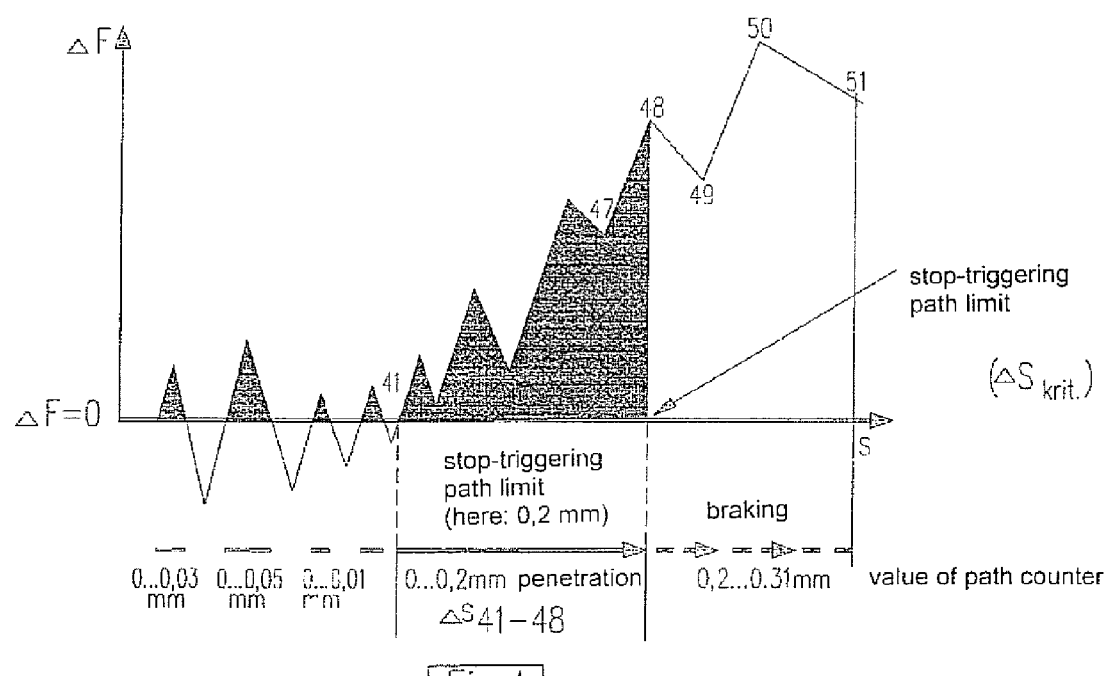
Figure 5:
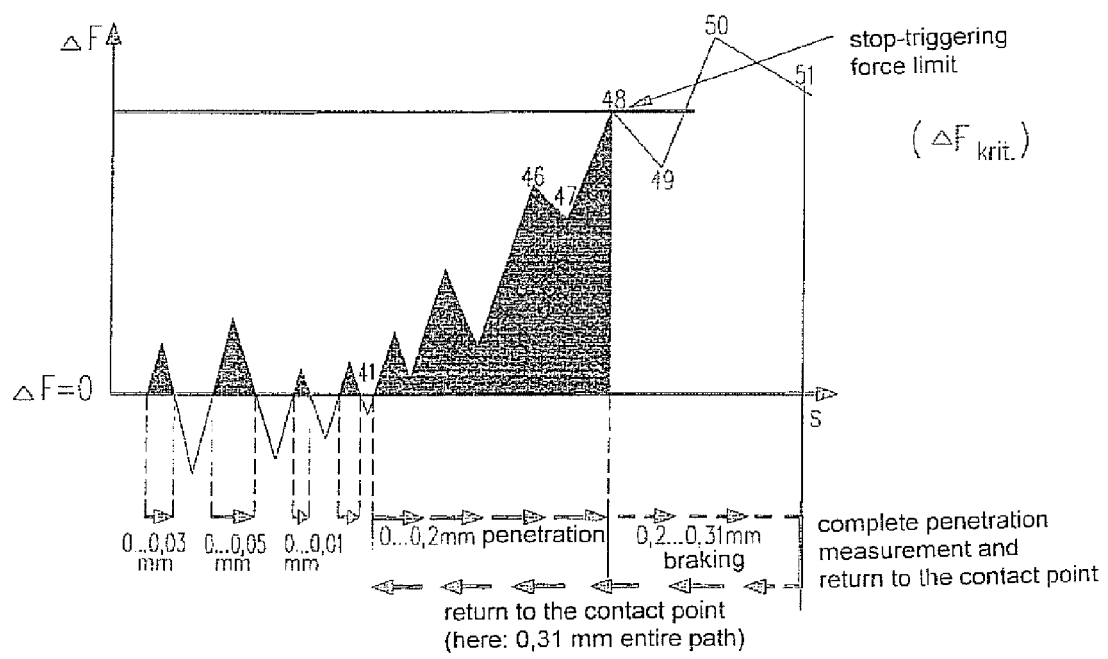

FIG. 1: shows a penetrometer according to the prior art,

FIG. 2: shows a schematic illustration of a measuring body having an integrated force/path sensor of a penetrometer according to the present invention, FIG. 3: shows a diagram, which depicts force differences measured by the force/path sensor depending on the time as well as values of a time counter, wherein a predetermined time limit of the time counter of 20 ms is used as the abortion criterion, FIG. 4: shows a diagram, which depicts force differences of the force/path sensor depending on the path of the measuring body and values of a path counter, wherein a predetermined path of the path counter of 0.2 mm is used as the abortion criterion, and FIG. 5: shows a diagram, which depicts force differences measured by the force/path sensor depending on the path of the measuring body and values of the path counter, wherein a predetermined force difference of the force/path sensor of $\Delta F_{krit}$ is used as the abortion as the criterion.

FIG. 1 shows a penetrometer for the determination of the degree of hardness of semisolid material according to the prior art. For performing the measurement, the penetrometer is placed over the test material. Preferably petroleum products such as bitumen are used as semisolid materials. Further semisolid materials may be for example products of the foot industry, the package industry, cosmetic and chemical products and the like. The penetrometer comprises of falling rod 5 having a penetration body 8 (e.g. a needle) which are adapted in the preferred embodiment for the determination of hardness of bitumen. For the determination of the degree of hardness, the falling rod 5 (with the penetration body 8) is moved downwards by means of the handwheels 2, 4 for contacting the surface of the test material until the tip of the measuring body contacts the test material. This position is called the starting position of the measurement. The exact determination of the starting position may be difficult because the visibility in the portion of the contact point may be relatively bad and the subjective perception of the user of the penetrometer may result in errors. For an improvement of the visibility, the penetrometer of the prior art comprises a lamp 1 and a lens 7. It is not possible to determine the starting position with such a penetrometer according to a counter pressure resulting from the test material, because the measuring body 5, 8 would easily penetrate into the test material at low pressure which would afflict the determination of the starting position and therefore also afflict the penetration measurement. These measurement errors during the determination of the degree of hardness of semisolid test materials may be eliminated with a penetrometer according to the present invention. According to DE 102 57 170 B4 it is possible to adjust the starting position automatically and therefore it is no more necessary to manually adjust the starting position. According to the method of the present invention (FIG. 3-5), the touch-down point of the penetration body may be determined by use of the force/path sensor 20 more reliable and more simple compared to the method known from DE 102 57 180 B4. To this and, a measured force of the force/path sensor 20 is compared with an adjusted force value during the downward movement of the measuring body 5, 8, i.e. the measured force is compared with compensating static influences such as the weight of the measuring body and offset influences (the compensation may be realised e.g. in the analogue measuring signal by use of a capacitor filter). In case the lowering speed and the weight of the components to be moved downwards are known prior to conducting the measuring, it is also possible to use a reference value as the adjusted force value. Once the measured force (and therefore the determined force difference) increases during a uniform downward movement, while the adjusted measuring value is maintained and the measured force of consecutive measurements has the same algebraic sign, the absolute value of the measured force will significantly deviate from the previously measured values (which have changing algebraic signs when using a stepping motor) in case the measuring body 5, 8 will contact the surface of the test material. As soon as the determined force differences have a positive value, a time counter will be started (FIG. 3). This time counter measures a time during which the determined force differences (differences between the measured force values and the adjusted force value) comprise positive values (including zero), as for example during the time intervals $t_{25-27}$, $t_{29-31}$ and $t_{37-39}$ in FIG. 3. In case the determined force differences comprise negative values, the time counter is reset (to zero) and is restarted if the determined force differences comprise positive values. In the lower portion of FIG. 3, the values of the time counter are schematically depicted: a solid line means that the time counter has been started and the time is running. A missing line (negative force differences) means that the time counter is in a reset state (value of time counter is zero), and the length of the respective lines schematically shows the maximum values of the time counter before being reset. In point 25, a time and path counting starts according to the slide drive of the downward moving sensor 20. The path counter increases up to point 27 and thereby determines a value of e.g. 0.03 mm (FIG. 4), i.e. the sensor 20 has passed a distance of 0.03 mm during the time interval of point 25 to point 27. At point 27 said counting is stopped and reset to 0 mm (analogously the time counter in FIG. 3 is reset to 0 sec.) because the force value differences have negative values. Due to the fact that the force difference values are negative up to point 29, the counter remains in a reset state. The negative force difference values indicate that the previously determined positive force difference values resulted from an interference (disturbance) which is judged as not being valid and therefore discarded. The contacting of the measuring body with the surface of the test material would however result in a permanent positive signal. The procedure is repeated from point 29 such that the path counter determines a path up to point 31 and then the path counter is again reset due to a further interference.

As soon as the measuring body contacts the surface 21 of the test material 22 (FIG. 2) during the downward movement (in the preferred embodiment during the point in time $t_{41}$), the time (and/or the further path by means of a path counter such as a coding disc/path counting combination) is registered by the time counter. In case the algebraic sign of consecutive force differences is continuously the same, the abortion criterion will be met in the point in time $t_{48}$ because the time counter exceeds or reaches a predetermined value (here 20 ms). In this moment, a breaking from $t_{48-51}$ is carried out and the measuring body is reset to a position (s41) (exact starting position) in which the time counter previously started. Then the real measurement of the degree of hardness may start. In the present embodiment, the exact starting point is point 41. From this point on, the algebraic signs of the increasing force remains to be the same and therefore the time counter and the path counter will no more be reset. In point 48 the time (FIG. 3), the path (FIG. 4) and/or the force difference (FIG. 5) exceeds a predetermined limit which results in an interruption of the downward movement of the measuring body (any interference of this amount will also interrupt said downward movement). The path which the measuring body has traveled during point 41 and point 48 (point means point in time) is e.g. 0.20 mm. The slide will travel a bit further due to its inertia up the absolute stop (=point 51). The additional path up to the final stop is again e.g. 0.11 mm. Therefore in the time counter the complete difference between point 41 and point 51, that means here 0.2 mm+0.11 mm=0.31 mm is stored. The slide has now to be reset by a distance of 0.31 mm in order to return to the first registered contact point (exact contact point 41). Thus, this analysis discards all previous invalid distance countings; only the path counting during the permanently positive force signal until the abortion criterion is met (time-, path- or force difference limit) is taken into account for the determination of the required reset path which is necessary for returning to the contact point.

Using the above means and methods it is advantageous that electronic and/or mechanical interferences (such as positive and negative acceleration forces during lowering due to a step motor, which result in accelerating force differences such as $\Delta F_{42-48}$) may be eliminated or the method according to the invention has a lower sensitivity with respect to such interference. The selection of the abortion criterion may be made in accordance with the material to be tested and to device parameters (weight of the measuring body etc.).

Instead of using a predetermining time period as an abortion criterion (FIG. 3) it is alternatively possible to use a predetermined force difference value $\Delta F_{krit}$ (see FIG. 5) or a predetermined path (FIG. 4) as an abortion criterion. Said force difference value $\Delta F_{krit}$ has no influence on the exact determination of the contact point because the contact point is already "prebooked" by relinquishing the zero force line by the time counter (FIG. 3) and/or by the path counter (FIGS. 4 and 5). Due to the logic of time restriction (FIG. 3) and/or path restriction (FIG. 4) after leaving the zero force line ($F_{Ber}$), an unwanted penetration of the measuring body 5, 8 into the test material 22 can be avoided which would negatively influence the subsequent penetration measurement due to crater formation. The time period until braking is therefore preferably determined in accordance with device and material characteristics prior to the measurement (braking deceleration) and an advantage of the method according to the invention is that unwanted electronic and mechanic interferences may not result as much as incorrect measurements as they do in the prior art methods. It is thereby taken into account that disruption signals more or less comprise periodical zero points which reset and restart a path counter (or a time counter) within a critical residual time at each zero point and thereby do not result in a braking process. Only in case of exceeding a critical time (FIG. 3), a critical path (FIG. 4) and/or a critical force difference (FIG. 5), a braking process is carried out and the registered path ($S_{41-51}$) from the beginning of counting until the complete stop is used for returning to the exact starting position ($S_{41}$, 21).

A further advantage of the device of the present invention is that a force measurement for determining the starting position is consulted only one time and therefore the interference only influences the force measurement one time. A further improvement is realized in that no usually necessary security threshold value for triggering the braking process is necessary but the measuring sensitivity is optimal in accordance with this interference automatically.

FIG. 2 schematically depicts a measuring body 5, 8 having an integrated force/path sensor 20 of a penetrometer according to the present invention. Unwanted masses that influence the force/path sensor 20 may be reduced due to the integration of the force/path sensor 20 into the falling rod 5. The falling rod 5 (in which of the penetration needle is fixed) is fixed via the falling rod interlock 6, wherein the falling rod interlock 6 is fixed above the test material (not here depicted). The vertical position of the measuring body 5, 8 is controlled by the step motor 4 which is connected with the analysis-control unit 27. A wire-bound or a wireless data transmission is provided between the analysis-control unit 27 and the force/path sensor 20.

The power supply which is necessary for the force/path sensor 20 as well as the resulting measuring signals from the force/path sensor 20 may be transmitted via electrical contacts or contactlessly via electromagnetic waves to the analysis and control means. The signal transmission shall not afflict the penetration due to unwanted friction and therefore the contacting preferably (automatically) pivots away after the adjustment of the starting position but before the penetration measurement.

LIST OF REFERENCE SIGNS 1 spotlight
2 rough adjustment
3 sensor for path recording
4 step motor/fine adjustment of height
5 measuring body/falling rod
6 falling rod interlock
7 lens
8 measuring body/penetration needle
9 control panel
10 display
20 force/path sensor
21 exact position of the surface of the test material
22 test material/material to be measured
23 penetration depth
24 electrical contact of the force/path sensor
25 means for horizontal movement
26 electrical contact of analysis unit
27 analysis- and control unit

The invention claimed is:

1. Method for determination of the degree of hardness of semisolid materials (22) by measurement of the penetration depth (23) of a measuring body (5, 8) which is dropped into the material to be tested under its own weight, wherein prior to the penetration measurement the measuring body (5, 8) which is connected to a force/path sensor (20) is moved downwards from a initial position ($S_{25}$) which is located above the test material (22) to a return point ($S_{51}$) which is located within the test material (22), and the exact starting position (21, $s_{41}$) of the surface of the test material (22) is determined and the measuring body (5, 8) is arranged in the determined starting position (21, $s_{41}$), characterized in that
an adjusted force value ($F_{Ber}$) is determined prior or during the downward movement of the force/path sensor (20) from the initial position ($S_{25}$) to the return point ($S_{51}$) and for a plurality points in time ($t_{32\text{-}48}$) the force difference ($\Delta F_{32}$–$\Delta F_{48}$) between the adjusted force value ($F_{Ber}$) and the measured force value ($F_{32}$–$F_{48}$) of the respective point in time ($\Delta F_{32}$–$\Delta F_{48}$) is determined and furthermore a zero time ($t_{41}$) is determined for which at least one of the following criteria i)-iii) is met:
i) the force differences of consecutive measurements have the same algebraic sign effective from the zero time ($t_{41}$) and the time difference between the zero time ($t_{41}$) and one of the consecutive measurements exceeds a predetermined time limit,
ii) the force differences of consecutive measurement have the same algebraic signs effective from the zero time ($t_{41}$) and the force difference of a measurement after the zero times ($t_{41}$) exceeds a predetermined force value,
iii) the force differences of consecutive measurements have the same algebraic sign effective from the zero time ($t_{41}$) and a path difference between the zero time ($t_{41}$) path value and one of the consecutive measurements exceeds a predetermined path limit,
wherein the position (21, $s_{41}$) of the measuring body (5, 8) at the zero time ($t_{41}$) is used as the exact starting position (21, $s_{41}$) of the surface of the test material (22).

2. The method according to claim 1, characterized in that
a time interval is divided into a plurality of points in time for the determination of an adjusted force measurement value, wherein the time interval is located after the start of the downward movement of the measuring body (5, 8) until the arrival of the return point, wherein the respective force values are measured for a given number of consecutive measuring times during which the measuring body (5, 8) is located above the semisolid material and an adjusted force value is determined as an arithmetic mean of the measured force values.

3. The method according to claim 2, characterized in that
the adjusted force value ($F_{Ber}$) is additionally determined in accordance with the lowering velocity of the measuring body (5, 8).

4. The method according to claim 1, characterized in that
a reference value is used for the determination of the adjusted force value ($F_{Ber}$).

5. The method according to claim 4, characterized in that
the reference value is selected in accordance with the weight of the measuring body (5, 8) and the lowering velocity of the measuring body (5, 8).

6. The method according to claim 1, characterized in that
a step motor (4) is used for lowering the measuring body (5, 8) into the material to be measured (22).

7. The method according to claim 1, characterized in that
a material (22) is used comprising a needle penetration (8) value ranging from 5 to 500 according to ASTM D5.

8. The method according to claim 7, characterized in that
the lowering of the measuring body (5, 8) into the test material (22) is carried out such marginally that only an elastic deformation results in the test material (22) due to the penetration of the measuring body (5, 8) up to the return point.

9. The method according to claim 1, characterized in that
a test material (22) is used having a working penetration value according to ASTM D217 ranging from 50 to 500.

10. The method according to claim 9, characterized in that
the measuring body (5, 8) is lowered such into the test material (22) that the test material (22) is inelastically deformed due to the penetration of the measuring body (5, 8) up to the return point.

11. The method according to claim 1, characterized in that the time limit ($\Delta t_{KRIT}$), the force ($\Delta F_{KRIT}$) limit or the path limit ($\Delta S_{KRIT}$) for the criteria i)-iii) is determined in accordance with the test material (22) and/or device parameters.

12. The method according to claim 1, characterized in that criterion ii) and at least one of criteria i) and iii) are met at the same time.

13. The method according to claim 1, characterized in that all of criteria i)-iii) are met at the same time.

14. A penetrometer for determining the degree of hardness of semisolid materials (22) comprising: a measuring body, a force/path sensor (20), means for a vertical movement of the measuring body and means (27) for analysis of the measurement values of the force/path sensor (20) and for controlling the means for vertical movement of the measuring body, wherein the measuring body comprises a falling rod (5) and a penetration body (8), wherein the measuring body is fixed by an interlock (6), wherein the interlock (6) is supported over the test material (22), and wherein the force/path sensor (20) is connected with the measuring body and the analysis and control means (27) comprises a data transmission to the force/path sensor (20) and to the means for vertical movements for the measuring body (20), characterized in that the force/path sensor (20) is arranged inside the falling rod (5).

15. The penetrometer according to claim 14, characterized in that the force/path sensor (20) is arranged in the lower portion of the falling rod (5).

16. The penetrometer to claim 14, characterized in that the force/path sensor (20) is arranged directly above the clamping for the penetration body (8).

17. The penetrometer according to claim 14, characterized in that the force/path sensor (20) comprises a first electrical contact (24) for data transmission and the analysis and control means (27) comprises a second electrical contact (26), wherein the electrical contacts (24, 26) are arranged side by side and the second electrical contact (26) is connected with a means for horizontal movement (25) of the second electrical contract (26) in order for contacting and decontacting with the first electrical contact (24).

18. The penetrometer according to claim 14, characterized in that means for wireless data transmission are provided between the force/path sensor (20) and the analysis and control unit (27) and/or between the analysis and control unit (27) and the means for vertical movements for the measuring body.

19. The penetrometer according to claim 18, characterized in that the means for wireless data transmission between the force/path sensor (20) and the analysis and control unit (27) comprises a transponder, wherein the transponder is integrated within the force/path sensor (20) or wherein the transponder is integrated in the falling rod (5) and connected with the force/path sensor (20).

20. The penetrometer according to claim 14, characterized in that the means for vertical movement of the measuring body (5, 8) is a step motor.

21. The penetrometer according to claim 14, characterized in that the analysis and control unit (27) is formed of a computer or is formed of a plurality of separate modules.

* * * * *